United States Patent
Lobo et al.

(10) Patent No.: US 12,121,689 B2
(45) Date of Patent: Oct. 22, 2024

(54) SURGICAL ACCESS DEVICE HAVING A HOLLOW ANCHOR

(71) Applicant: Covidien LP, Mansfield, MA (US)

(72) Inventors: Astley C. Lobo, West Haven, CT (US); Kevin M. Desjardin, Prospect, CT (US); Christopher A. Tokarz, Wallingford, CT (US); Douglas M. Pattison, Bristol, CT (US)

(73) Assignee: Covidien LP, Mansfield, MA (US)

( * ) Notice: Subject to any disclaimer, the term of this patent is extended or adjusted under 35 U.S.C. 154(b) by 843 days.

(21) Appl. No.: 17/246,983

(22) Filed: May 3, 2021

(65) Prior Publication Data
US 2022/0347454 A1   Nov. 3, 2022

(51) Int. Cl.
*A61B 17/34* (2006.01)
*A61M 39/02* (2006.01)

(52) U.S. Cl.
CPC ..... *A61M 39/0247* (2013.01); *A61B 17/3423* (2013.01); *A61M 2039/0279* (2013.01); *A61M 2039/0285* (2013.01)

(58) Field of Classification Search
CPC ............ A61B 17/3417; A61B 17/3421; A61B 17/3423; A61B 2017/3419; A61B 2017/348; A61B 2017/3482; A61B 2017/3484; A61B 2017/3486; A61B 2017/3488; A61B 2017/349; A61B 2017/3492; A61B 2017/00889; A61B 2217/007; A61M 1/85; A61M 2039/025; A61M 2025/0056
See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

Extended European Search Report dated Aug. 18, 2022, issused in corresponding EP Appln. No. 22170991.8.

(Continued)

*Primary Examiner* — Diane D Yabut
(74) *Attorney, Agent, or Firm* — Draft Masters IP, LLC

(57) ABSTRACT

A surgical access device has a housing and a tubular member extending from the housing. A collar includes proximal and distal walls along with first and second sidewalls. The first and second sidewalls have a circular configuration and join the proximal and distal walls. The collar is repositionable along a length of the tubular member. A cavity is defined between the proximal and distal walls and the first and second sidewalls. The cavity is configured to store a quantity of a fluid therein. Pores extend through the distal wall and each pore is configured to allow a predetermined quantity of the fluid to flow therethrough. A port is disposed through the proximal wall and is in fluid communication with the cavity. The port is configured to allow the fluid to be introduced into the cavity.

20 Claims, 5 Drawing Sheets

(56) References Cited

U.S. PATENT DOCUMENTS

| | | |
|---|---|---|
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,300,448 B2 | 11/2007 | Criscuolo et al. |
| 7,691,089 B2 | 4/2010 | Gresham |

(56) References Cited

U.S. PATENT DOCUMENTS

| | | |
|---|---|---|
| 8,454,645 B2 | 6/2013 | Criscuolo et al. |
| 8,926,508 B2 | 1/2015 | Hotter |
| 10,022,149 B2 | 7/2018 | Holsten et al. |
| 2011/0144447 A1 | 6/2011 | Schleitweiler et al. |
| 2014/0343366 A1 | 11/2014 | Coe et al. |

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2016186905 A1 | 11/2016 |

OTHER PUBLICATIONS

European Office Action dated Feb. 20, 2024, issued in corresponding EP Appln. No. 22170991, 6 pages.

SURGICAL ACCESS DEVICE HAVING A HOLLOW ANCHOR

FIELD

The present disclosure generally relates to a surgical access device. In particular, the present disclosure relates to a surgical access device having a hollow anchor that is capable of storing a fluid therein.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the minimally invasive surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula.

An additional consideration during a minimally invasive procedure is reducing the risk of a port site infection. Typically, a clinician may apply an antibacterial solution directly to the port site. However, this approach is a single use application of the antibacterial solution. A more controlled and continuous application of the antibacterial solution would provide additional benefits.

SUMMARY

In accordance with an aspect of the present disclosure, a surgical access device has a housing, a tubular member extending distally from the housing, and a collar repositionable along the tubular member. The collar has a proximal wall, a distal wall, and first and second sidewalls with a circular configuration. The first and second sidewalls join the proximal and distal walls thereby defining a circular configuration of the collar. A cavity is defined between the proximal wall, the distal wall, the first sidewall, and the second sidewall and is configured to store a quantity of a fluid therein. Pores extend through the distal wall and each pore is configured to allow a predetermined quantity of the fluid to flow therethrough. A port is disposed through the proximal wall and is in fluid communication with the cavity. The port is configured to allow the fluid to be introduced into the cavity.

In aspects of the present disclosure, the fluid may be an antimicrobial liquid.

In an aspect of the present disclosure, the proximal and distal walls may have coincident central openings that, in combination with the first sidewall, define a lumen of the collar. The lumen may be configured to slidably receive the tubular member therethrough.

In a further aspect of the present disclosure, the pores may be circumferentially arranged proximate the central opening of the distal wall.

In aspects of the present disclosure, the fluid may be introduced into the cavity through the port with a syringe.

In another aspect of the present disclosure, the surgical access device may further include a membrane releasably attached to the distal wall of the collar. The membrane may be configured to cover the pores of the distal wall.

In an aspect of the present disclosure, the cavity of the collar may be filled with a quantity of the fluid.

In accordance with another aspect of the present disclosure, a surgical access device includes a housing, a cannula extending from the housing, and a collar surrounding the cannula and slidably disposed thereon. The collar includes a proximal wall, a distal wall, and opposed first and second sidewalls joining the proximal and distal walls. A cavity is defined between the proximal wall, the distal wall, and the opposed sidewalls. The cavity is configured to store a quantity of a fluid therein. Pores extend through the distal wall and each pore is configured to allow a predetermined quantity of the fluid to flow therethrough.

In an aspect of the present disclosure, the first and second sidewalls may have a circular configuration thereby defining a circular configuration of the collar.

In another aspect of the present disclosure, the proximal and distal walls may have coincident central openings that, in combination with the first sidewall, define a lumen of the collar. The lumen may be configured to slidably receive the cannula therethrough.

In aspects of the present disclosure, the fluid may be an antimicrobial liquid.

In a further aspect of the present disclosure, the surgical access device may include a port disposed through the proximal wall and in fluid communication with the cavity. The port may be configured to allow the fluid to be introduced into the cavity.

In an aspect of the present disclosure, the fluid may be introduced into the cavity through the port with a syringe.

In aspects of the present disclosure, the collar may include a membrane releasably attached to the distal wall of the collar. The membrane may be configured to cover the pores of the distal wall.

In another aspect of the present disclosure, the cavity of the collar may be filled with a quantity of the fluid.

In accordance with an aspect of the present disclosure, a method of assembling a surgical access device includes joining a tubular member to a housing and sliding a collar onto the tubular member. The collar includes opposed proximal and distal walls and first and second sidewalls having a circular configuration. The first and second sidewalls join the proximal and distal walls. A cavity is defined between the proximal wall, the distal wall, the first sidewall, and the second sidewall. A port is disposed through the proximal wall and is in fluid communication with the cavity. The port is configured to allow a fluid to be introduced into the cavity. Pores extend through the distal wall and each pore is configured to allow the fluid to flow therethrough.

In aspects of the present disclosure, the method may also include introducing the fluid into the cavity through the port with a syringe.

In another aspect of the present disclosure, introducing the fluid into the cavity may include the fluid being an antimicrobial liquid.

In an aspect of the present disclosure, sliding the collar onto the tubular member may include the pores being circumferentially disposed about the tubular member.

In a further aspect of the present disclosure, the method may further include removing a membrane that is releasably attached to the distal wall of the collar thereby exposing the pores of the distal wall.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
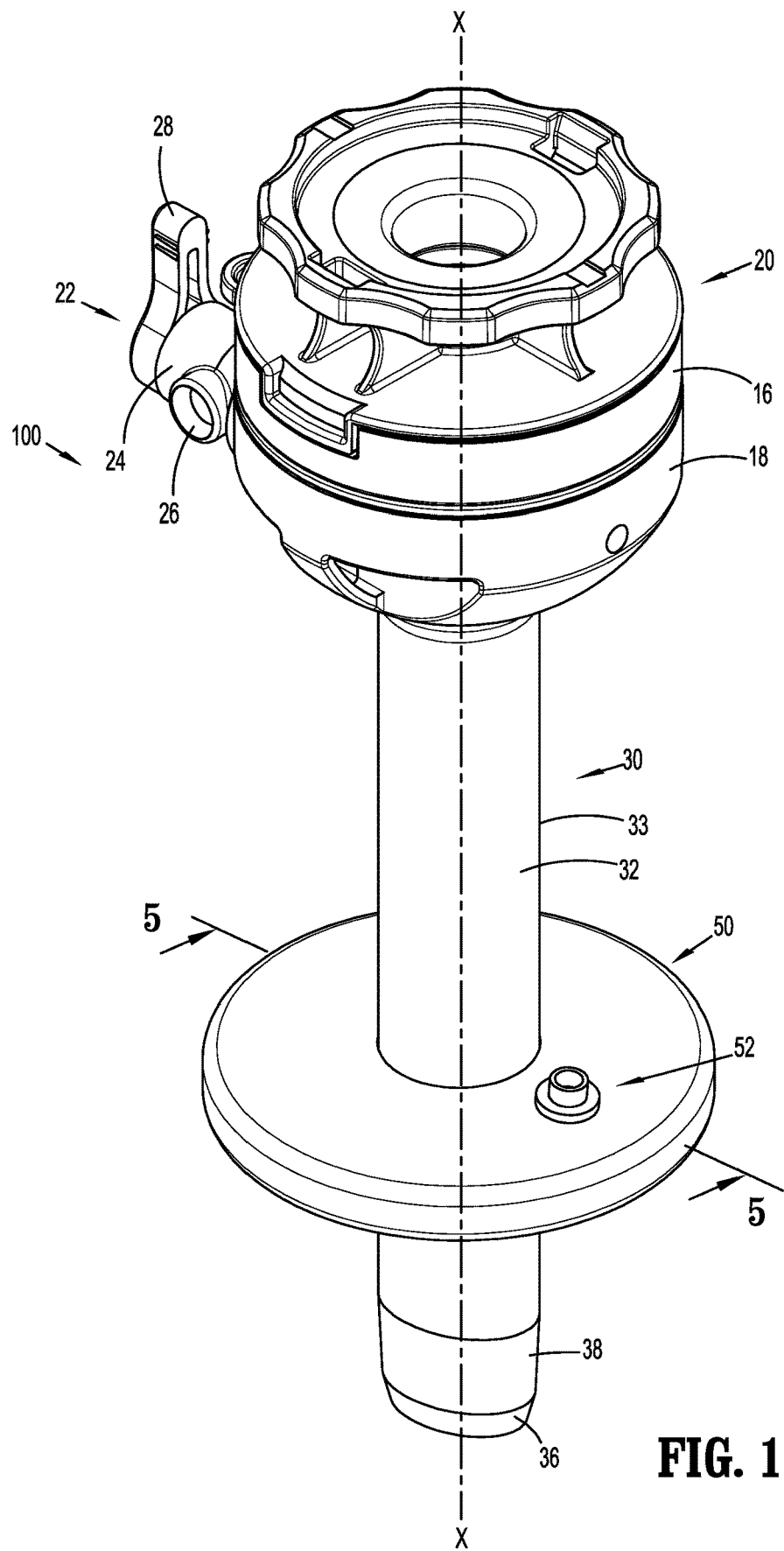
FIG. 1 is a perspective view of a surgical access device according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings.

Figure 2:
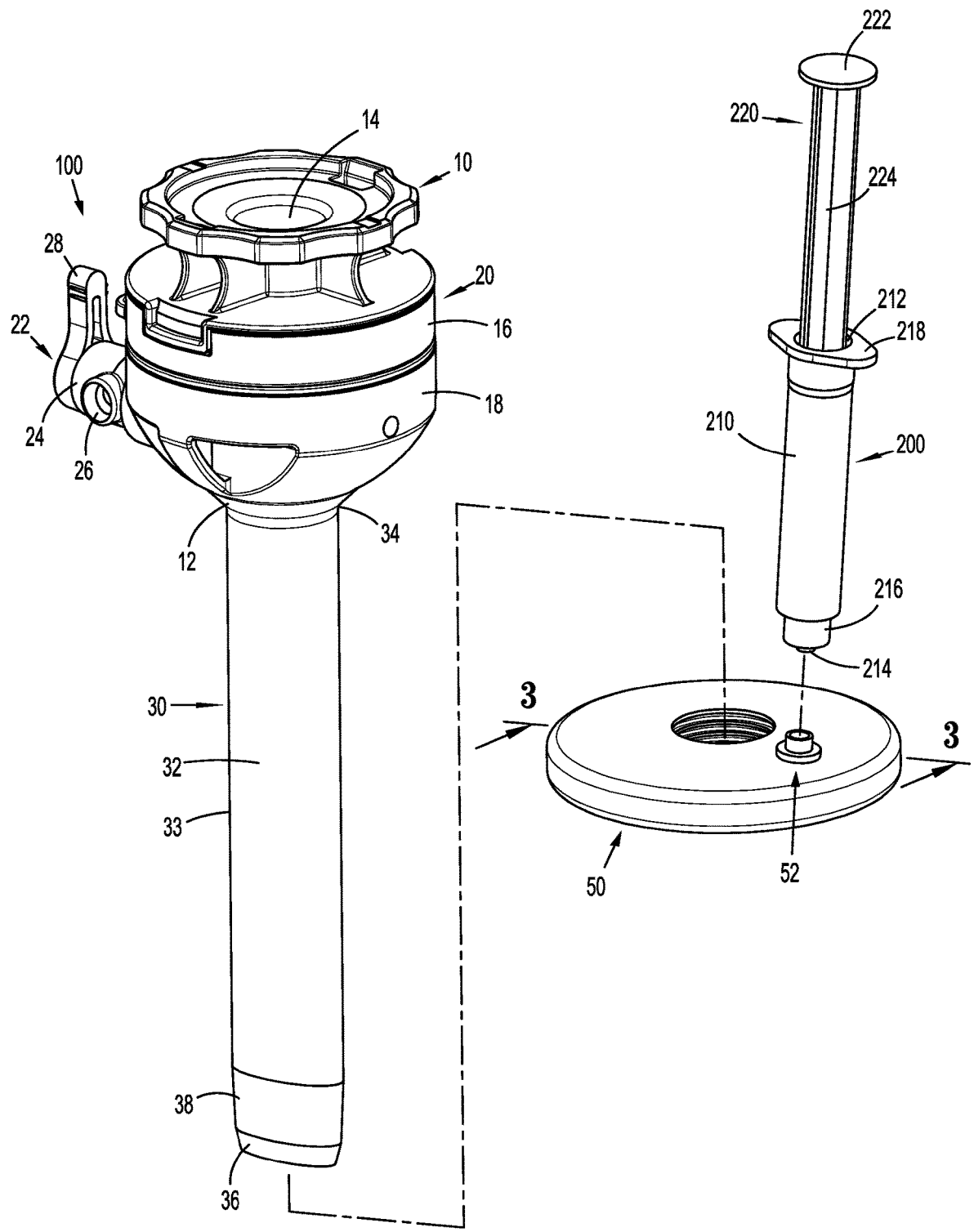
FIG. 2 is an exploded view, with parts separated, of the surgical access device of FIG. 1 with a syringe.
Figure 5:
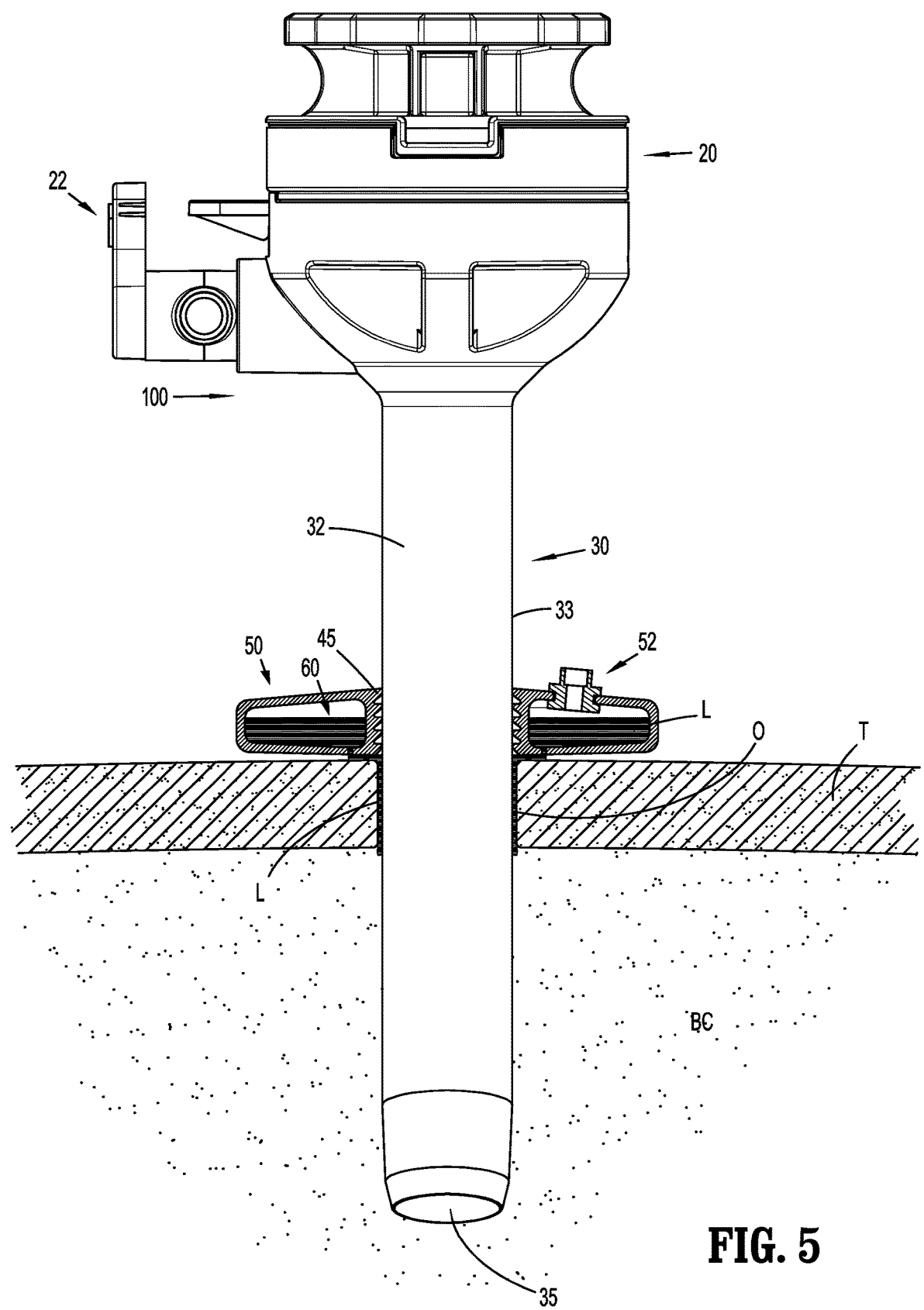
FIG. 5 is a side cross-sectional view of the surgical access device of FIG. 1 taken along section line 5-5 and positioned in a patient.

With initial reference to FIGS. 1 and 2, the presently disclosed surgical access device is shown and identified as surgical access device 100. The surgical access device 100 includes a housing 20 and a cannula or tubular member 30 extending from the housing 20. The tubular member 30 generally includes an elongated shaft 32 extending along a longitudinal axis "X." A proximal end portion 34 of the tubular member 30 is attached to a distal end 12 of the housing 20 and a distal end portion 36 of the tubular member 30 supports a balloon 38. The elongated shaft 32 includes a lumen 35 (FIG. 5) that extends along the longitudinal axis "X" of the tubular member 30 for reception and passage of a surgical instrument (not shown) therethrough. The housing 20 has an opening 14 at its proximal end 10 that allows insertion of a surgical instrument (not shown) therethrough. As such, a clinician is able to perform a surgical procedure at a work site in a body cavity "BC" that is beneath tissue "T" (FIG. 5). Examples of surgical instruments include, but are not limited to, graspers, staplers, endoscopes, etc. The housing 20 includes an upper housing section 16 and a lower housing section 18. The upper housing section 16 may be selectively attachable to, and detachable from, the lower housing section 18. In aspects, either or both of the upper and lower housing sections 16, 18 of the housing 20 may include knurls, indentations, tabs, or be otherwise configured to facilitate engagement by a user. The housing 20 supports a seal assembly (not shown) and a valve assembly (not shown). The seal assembly is disposed proximally of the valve assembly. The seal assembly generally includes an instrument seal for sealing around surgical instruments inserted through the housing 20 and into the tubular member 30. The valve assembly generally includes a zero-closure seal for sealing a lumen of the housing 20 in the absence of a surgical instrument inserted through the housing 20. The seal assembly and the valve assembly prevent the escape of the insufflation fluids therefrom, while allowing surgical instruments to be inserted therethrough and into the body cavity "BC". The instrument seal may include any known instrument seal used in tubular members and/or trocars, such as a septum seal. The zero-closure seal may be any known zero-closure seal for closing off the passageway into the lumen, such as a duckbill seal or flapper valve.

The housing 20 also includes an insufflation valve 22 coupled to the lower housing section 18. The insufflation valve 22 has a body 24 with a fitting 26 (e.g., luer connection) that is in fluid communication with a cavity of the housing 20 which, in turn, is in fluid communication with the lumen 35 of the tubular member 30 to insufflate a body cavity "BC", such as an abdominal cavity (e.g., create a pneumoperitoneum). The insufflation valve 22 is connectable to a source of insufflation fluid (not shown) using the fitting 26 for delivery of the insufflation fluid (e.g., $CO_2$) into the body cavity "BC" thereby separating layers of body tissue and creating a working site. In aspects, and as shown, the insufflation valve 22 is a stopcock valve for controlling the flow of the insufflation fluid. The insufflation valve 22, however, may be any known valve for directing fluid flow and, in some aspects, regulating fluid flow. A valve handle 28 is rotatable between an open position and a closed position. For a detailed description of the structure and function of components of exemplary surgical access assemblies, surgical access devices, and/or retention collars, reference may be made to commonly owned U.S. Pat. Nos. 7,300,448; 7,691,089; 8,926,508; and 10,022,149 the entire disclosures of which are hereby incorporated by reference.

Figure 3:
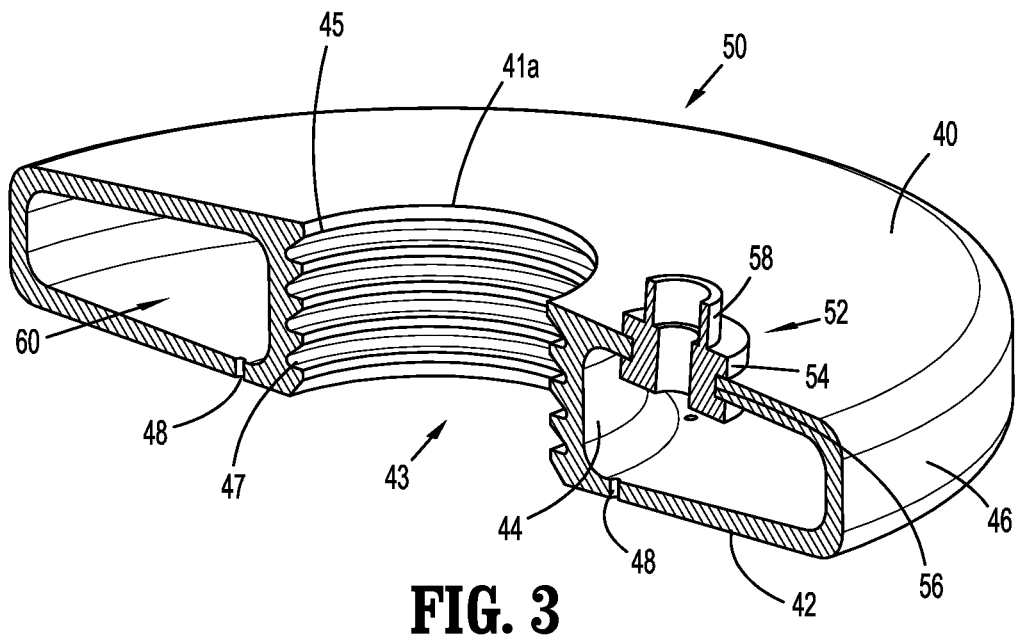
FIG. 3 is a perspective cross-sectional view of a collar of the surgical access device of FIG. 2 taken along section line 3-3.
Figure 4:
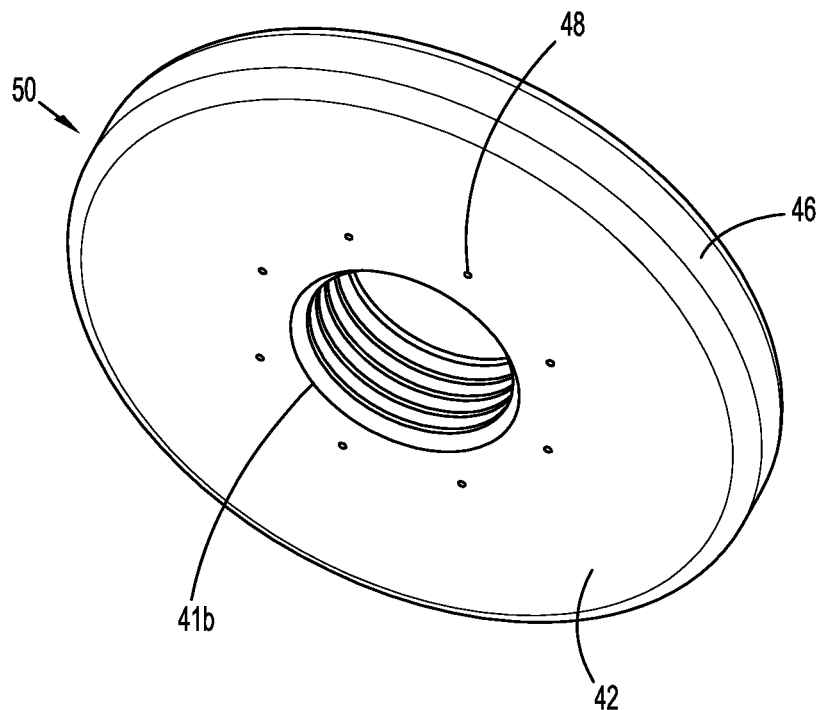
FIG. 4 is a bottom perspective view of the collar of the surgical access device of FIGS. 1 and 2.

As seen in FIG. 1, a collar 50 is supported on the elongated shaft 32 of the tubular member 30. The collar 50 is releasably engageable with the elongated shaft 32, and slidable therealong to adjust the longitudinal position of the collar 50 on the elongated shaft 32. The collar 50 contacts an outer surface of tissue "T" thereby facilitating securement of the surgical access device 100 (see e.g., FIG. 5). The collar 50 may be formed from an elastomeric material (e.g., rubber or silicone) to aid in sealing an opening "O" through tissue "T" and/or to aid in the collar in conforming to a surface contour of tissue "T". With additional reference to FIGS. 3 and 4, the collar 50 includes a top or proximal wall 40, a bottom or distal wall 42, and opposed first and second sidewalls 44, 46. Each of the proximal and distal walls 40, 42 has a circular configuration with a central opening 41a, 41b extending therethrough. The central openings 41a, 41b of the proximal and distal walls 40, 42 are coincident. Each of the proximal and distal walls 40, 42 has a generally planar configuration and may have a slightly arcuate or bowed shape when viewed in cross-section as shown in FIG. 3. The distal wall 42 includes pores 48 extending therethrough with each pore 48 having a diameter that is selected to allow a particular flow rate of a fluid through the pore 48. The flow rate through each pore 48 is a function of the diameter of the pore 48, the density of the fluid, the flow coefficient of the fluid, and the pressure differential across the distal wall 42. The pores 48 are distributed in a circular pattern on the distal wall 42 and circumscribe the central opening 41b of the distal wall 42. The pores 48 are shown as being generally uniformly spaced about the central opening 41b of the distal wall 42 and it is contemplated that other arrangements are possible. The first sidewall or inner wall 44 has a circular configuration with an alternating pattern of ribs 45 and grooves 47. The ribs 45 are configured to frictionally engage an outer surface 33 of the elongated shaft 32 of the tubular member 30 (FIG. 5), which allows a user to slide the collar 50 proximally and distally along the tubular member 30. In the absence of user intervention, the interaction between the ribs 45 and the outer surface 33 retains a position of the collar 50 on the tubular member 30. The first sidewall 44 extends from the central opening 41a of the proximal wall 40 to the central opening 41b of the distal wall 42 and has a generally cylindrical shape. The second sidewall or outer wall 46 has a circular configuration and extends from an outer edge of the proximal wall 40 to an outer edge of the distal wall 42. Thus, the proximal wall 40, the distal wall 42, and the opposed first and second sidewalls 44, 46 define a circular configuration of the collar 50. Further, a chamber or cavity 60 is defined between the proximal wall 40, the distal wall 42, and the opposed first and second sidewalls 44, 46. The cavity 60 is configured to store a quantity of a fluid therein. A port 52 extends through an orifice 49 in the proximal wall 40. The port 52 is open and allows fluid communication between the cavity 60 and the ambient environment surrounding the collar 50. Thus, fluid may be added to the cavity 60 through the port 52. The port 52 has a sleeve 54 with a groove 56 that circumscribes the sleeve 54. The groove 56 is dimensioned to receive a portion of the proximal wall 40 therein thereby frictionally coupling the port 52 to the proximal wall 40. A neck 58 of the sleeve 54 extends proximally and is configured to releasably couple with a syringe 200 (FIG. 2) as will be described in detail hereinbelow.

Referring back to FIG. 2, the syringe 200 includes a barrel 210 and a plunger 220. The barrel 210 has a proximal opening 212 leading into a chamber of the barrel 210. The chamber is configured to slidably receive the plunger therein 220. A distal opening is located at a distal end of an extension 214 of the barrel 210. The extension 214 has a smaller outside diameter than that of the barrel 210. Additionally, a shroud 216 circumscribes the extension 214 with a diameter greater than that of the extension 214 and less than that of the barrel 210. This arrangement between the shroud 216 and the extension 214 defines a recess that facilitates coupling the syringe 200 with the port 52 of the collar 50. The shroud 216 has an inner diameter approximately equal to an outer diameter of the neck 58 of the port 52. This arrangement provides a friction fit between the syringe 200 and the port 52. The extension 214 is dimensioned to fit inside the neck 58 of the port 52 which positions the distal opening of the extension 214 inside the sleeve 54 of the port 52 and in fluid communication with the cavity 60 of the collar 50. At the proximal end of the barrel 210 are wings 218 configured to facilitate grasping and operating the syringe 200 by the clinician. The plunger 220 has a proximal disc 222 configured to be engaged by finger or thumb of the clinician. The body of the plunger 220 has an X shaped cross-sectional configuration along a majority of its length defined by ribs 224. As assembled, the cylindrical section of the plunger 220 is inserted into the barrel 210 through the proximal opening 212. As the plunger 220 is translated distally through the barrel 210, a fluid (e.g., a liquid) disposed in the barrel 210 is discharged through the distal opening and into the cavity 60 of the collar 50. The fluid is a liquid antimicrobial solution using a suitable antimicrobial agent such as triclosan, chlorhexidine, tetracycline, polymyxin, aminoglycosides, penicillins, and other antimicrobial agents that can be delivered in liquid form. The syringe 200 may be used to fill the cavity 60 prior to use of the surgical access device 100, it may be used to fill the cavity 60 during use of the surgical access device 100, it may be used to add liquid to the cavity 60 during use of the surgical access device 100, or combinations thereof. Although the surgical access device 100 is shown with a syringe 200, it is contemplated that tubing with the correct dimensions may be coupled to the neck 58 of the port 52 to introduce liquid into the cavity 60.

Figure 6:
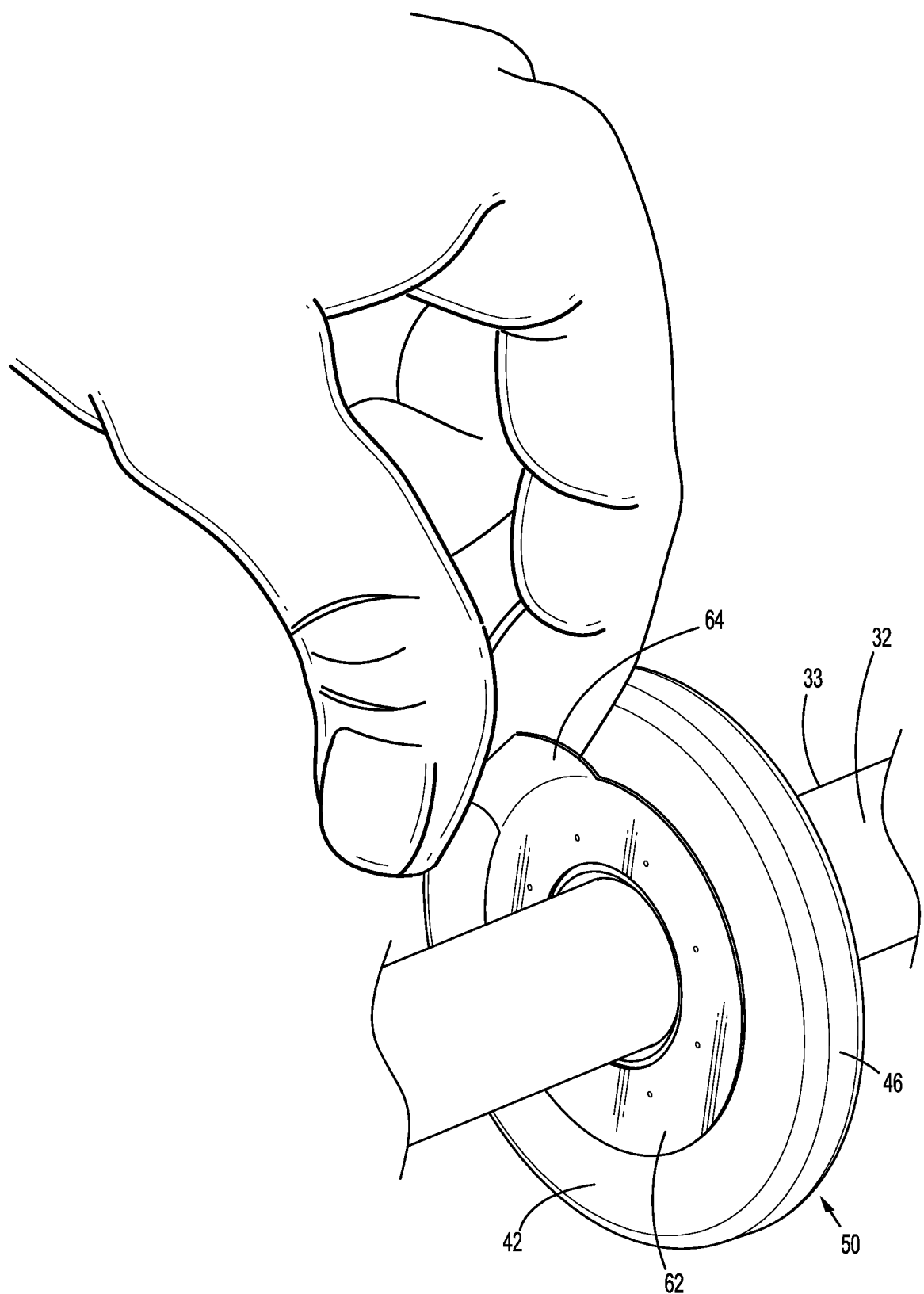
FIG. 6 is a bottom perspective view of a collar according to an aspect of the present disclosure illustrating removal of a membrane from a distal wall of the collar.

The cavity 60 of the collar 50 may be filled during a surgical procedure or may be filled prior to use by a clinician. In instances where the cavity 60 of the collar 50 is filled prior to use, a removable film or membrane 62 (FIG. 6) is attached to a bottom surface of the distal wall 42. It is contemplated that a cap (not shown) may cover a proximal opening of the neck 58 of the port 52 which prevents fluid loss through the port 52. The cap may be attached to the port 52 via a friction fit. By attaching the membrane 62 to the distal wall 42, the membrane 62 covers the pores 48 of the distal wall 42 so that any liquid stored in the cavity 60 lacks a flow path and is retained in the cavity 60. The membrane 62 has an annular configuration with a tab 64 extending radially outwards that facilitates a user removing the membrane 62 from the distal wall 42 of the collar 50 by providing a convenient location for grasping the membrane 62. The membrane 62 is formed from a polymeric material and attached to the bottom surface of the distal wall 42 using an adhesive.

Referring now to FIG. 5, the surgical access device 100 is illustrated with the tubular member 30 of the surgical access device 100 inserted through the opening "O" in tissue "T" such that the distal end portion 36 of the tubular member 30 is located at a surgical site within the body cavity "BC" of a patient. The collar 50 is translated distally along the tubular member 30 until the distal wall 42 of the collar 50 is in contact with an outer surface of tissue "T". In instances where the cavity 60 is pre-filled with an antibacterial liquid "L", the clinician grasps the tab 64 of the membrane 62 (FIG. 6) and removes the membrane 62 prior to inserting the tubular member 30 of the surgical access device 100 through the opening "O" in tissue "T". This exposes the pores 48 of the distal wall 42 and allows the antibacterial liquid "L" in the cavity 60 to pass through the pores 48. Once the tubular member 30 is positioned through the opening "O" in tissue "T" and the distal wall 42 of the collar 50 is in contact with the outer surface of tissue "T", the antibacterial liquid "L" flows through the pores 48, onto the outer surface of tissue "T", and into the opening "O" in tissue "T". In instances where the cavity 50 is empty prior to insertion, once the tubular member 30 of the surgical access device 100 is positioned through the opening "O" in tissue "T" and the distal wall 42 of the collar 50 is in contact with the outer surface of tissue "T", the clinician couples the syringe 200 containing the antibacterial liquid to the port 52 of the collar 50 as previously described and depresses the plunger 220 of the syringe 200 thereby adding the antibacterial liquid "L" to the cavity 60. Subsequently, the antibacterial liquid "L" flows through the pores 48 of the distal wall 42, onto the outer surface of tissue "T", and into the opening "O" in tissue "T". The clinician may refill the syringe 200 with additional antibacterial liquid or retrieve one or more additional syringes 200 with antibacterial liquid in instances where the initial quantity of antibacterial liquid is insufficient for the duration of the procedure. It is contemplated that the cavity 60 of the collar 50 may be pre-filled with a quantity of antibacterial liquid "L" and does not include the port 52 for adding additional antibacterial liquid to the cavity 60 of the collar 50. Once the surgical procedure is completed, the clinician removes the tubular member 30 of the surgical access device 100 from the opening "O" in tissue "T" and closes the opening "O" in tissue "T" using known techniques.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical access device comprising:
   a housing;
   a tubular member extending distally from the housing; and
   a collar repositionable along the tubular member, the collar having:
   a proximal wall,
   a distal wall,
   first and second sidewalls having a circular configuration, the first and second sidewalls joining the proximal and distal walls thereby defining a circular configuration of the collar,
   a cavity defined between the proximal wall, the distal wall, the first sidewall, and the second sidewall, the cavity configured to store a quantity of a fluid therein,
   pores extending through the distal wall, each pore configured to allow a predetermined quantity of the fluid to flow therethrough, and
   a port disposed through the proximal wall and in fluid communication with the cavity, the port configured to allow the fluid to be introduced into the cavity.

2. The surgical access device according to claim 1, wherein the fluid is an antimicrobial liquid.

3. The surgical access device according to claim 1, wherein the proximal and distal walls have coincident central openings that, in combination with the first sidewall, define a lumen of the collar, the lumen configured to slidably receive the tubular member therethrough.

4. The surgical access device according to claim 3, wherein the pores are circumferentially positioned proximate the central opening of the distal wall.

5. The surgical access device according to claim 1, wherein the fluid is introduced into the cavity through the port with a syringe.

6. The surgical access device according to claim 1, further including a membrane releasably attached to the distal wall of the collar, the membrane configured to cover the pores of the distal wall.

7. The surgical access device according to claim 6, wherein the cavity of the collar is filled with a quantity of the fluid.

8. A surgical access device comprising:
   a housing;
   a cannula extending from the housing; and
   a collar surrounding the cannula and slidably disposed thereon, the collar including:
   a proximal wall,
   a distal wall,
   first and second sidewalls joining the proximal and distal walls,
   a cavity defined between the proximal wall, the distal wall, and the opposed sidewalls, the cavity configured to store a quantity of a fluid therein, and
   pores extending through the distal wall, each pore configured to allow a predetermined quantity of the fluid to flow therethrough.

9. The surgical access device according to claim 8, wherein the first and second sidewalls have a circular configuration thereby defining a circular configuration of the collar.

10. The surgical access device according to claim 9, wherein the proximal and distal walls have coincident central openings that, in combination with the first sidewall, define a lumen of the collar, the lumen configured to slidably receive the cannula therethrough.

11. The surgical access device according to claim 8, wherein the fluid is an antimicrobial liquid.

12. The surgical access device according to claim 8, further including a port disposed through the proximal wall and in fluid communication with the cavity, the port configured to allow the fluid to be introduced into the cavity.

13. The surgical access device according to 12, wherein the fluid is introduced into the cavity through the port with a syringe.

14. The surgical access device according to claim 8, further including a membrane releasably attached to the distal wall of the collar, the membrane configured to cover the pores of the distal wall.

15. The surgical access device according to claim 14, wherein the cavity of the collar is filled with a quantity of the fluid.

16. A method of assembling a surgical access device comprising:
   joining a tubular member to a housing; and
   sliding a collar onto the tubular member, the collar including:
   opposed proximal and distal walls,
   first and second sidewalls having a circular configuration, the first and second sidewalls joining the proximal and distal walls,
   a cavity defined between the proximal wall, the distal wall, the first sidewall, and the second sidewall, a port disposed through the proximal wall and in fluid communication with the cavity, the port configured to allow a fluid to be introduced into the cavity, and pores extending through the distal wall, each pore configured to allow the fluid to flow therethrough.

17. The method according to claim 16, further including introducing the fluid into the cavity through the port with a syringe.

18. The method according to claim 17, wherein introducing the fluid into the cavity includes the fluid being an antimicrobial liquid.

19. The method according to claim 16, wherein sliding the collar onto the tubular member includes the pores being circumferentially disposed about the tubular member.

20. The method according to claim 16, further including removing a membrane that is releasably attached to the distal wall of the collar thereby exposing the pores of the distal wall.

* * * * *